(12) United States Patent
Paradis

(10) Patent No.: US 7,041,997 B2
(45) Date of Patent: May 9, 2006

(54) DEVICE AND METHOD FOR OPTICAL CONTROL UNDER DIFFUSE ILLUMINATION AND OBSERVATION MEANS OF CROCKERY ITEMS OR ANY GLAZED CERAMIC PRODUCTS

(75) Inventor: Francois Paradis, Riom (FR)

(73) Assignee: Optomachines, Riom (FR)

( * ) Notice: Subject to any disclaimer, the term of this patent is extended or adjusted under 35 U.S.C. 154(b) by 0 days.

(21) Appl. No.: 10/221,736

(22) PCT Filed: Mar. 13, 2001

(86) PCT No.: PCT/FR01/00752

§ 371 (c)(1),
(2), (4) Date: Dec. 18, 2002

(87) PCT Pub. No.: WO01/69214

PCT Pub. Date: Sep. 20, 2001

(65) Prior Publication Data

US 2003/0184740 A1    Oct. 2, 2003

(30) Foreign Application Priority Data

Mar. 14, 2000  (FR) .................................. 00 03410

(51) Int. Cl.
*G01N 21/86* (2006.01)
(52) U.S. Cl. ................ 250/559.16; 356/237.1
(58) Field of Classification Search .......... 250/559.42, 250/559.16–559.18, 559.04, 559.05; 356/239.4, 356/237.1; 348/126

See application file for complete search history.

(56) References Cited

U.S. PATENT DOCUMENTS

| 4,677,473 A | 6/1987 | Nakahara et al. ............ 348/126 |
| 4,972,092 A | 11/1990 | Schmitt et al. ........ 250/559.11 |
| 5,278,411 A | 1/1994 | Houston et al. ............ 250/330 |
| 5,461,417 A * | 10/1995 | White et al. ................ 348/131 |
| 5,644,140 A | 7/1997 | Biedermann et al. .. 250/559.08 |
| 5,917,602 A * | 6/1999 | Bonewitz et al. ........... 356/614 |

FOREIGN PATENT DOCUMENTS

| EP | 0 756 152 | 1/1997 |
| JP | 63-241408 A * | 10/1988 |
| WO | 94 28397 | 12/1994 |
| WO | 00 09271 | 2/2000 |

OTHER PUBLICATIONS

Patent Abstract of Japan vol. 012, No. 290-742), Aug. 9, 1988.
Patent Abstract of Japan 63 066445 A (Ikegami Tsushinki Co Ltd; Others: 01), Mar. 25, 1988.

* cited by examiner

*Primary Examiner*—Thanh X. Luu
(74) *Attorney, Agent, or Firm*—Arent Fox PLLC

(57) ABSTRACT

The invention concerns a method and a device for controlling the surface of ceramic tableware products/ceramic crockery items (and the like, in accordance with the general definition provided in the introduction). The invention is characterised in that it consists, with a single equipment, in: A) providing a global diffuse illumination for the whole or for zones of the products; B) observing the product, with one or more observation means, by reflection on the latter, towards the observation means, of the global diffuse illumination or localised diffuse illumination coming from at least one light-emitting zone adapted to provide brightness on at least a selected portion of the product. The invention enables to highlight and locate, with one single apparatus, all types of defects, in accordance with multi-purpose and efficient processes even concerning sensitive aspects such as complex shape conjunction, brightness, white dots on white background, which was not possible in prior art.

60 Claims, 10 Drawing Sheets

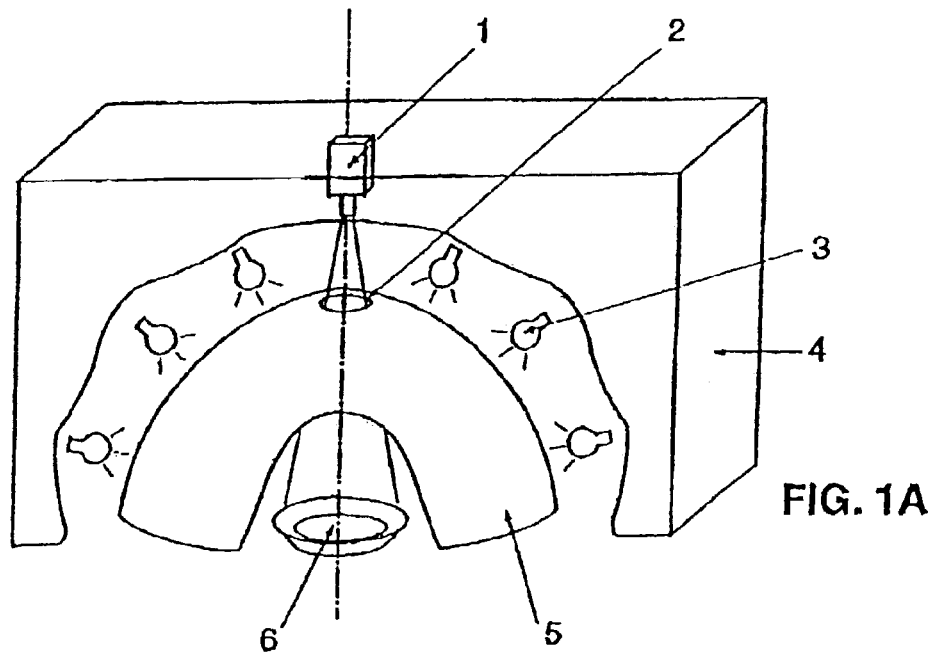
FIG. 1A
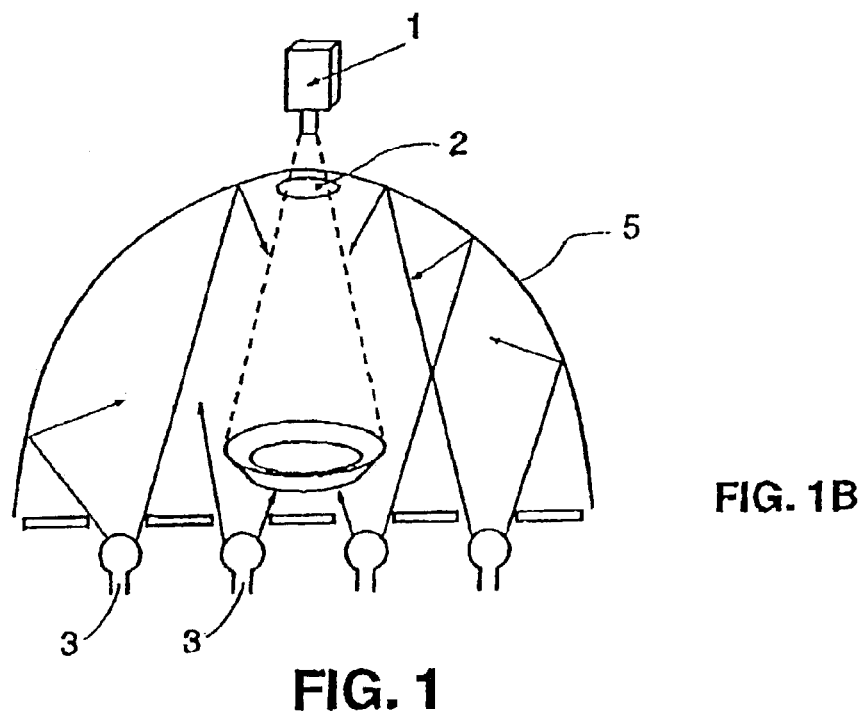
FIG. 1B
FIG. 1

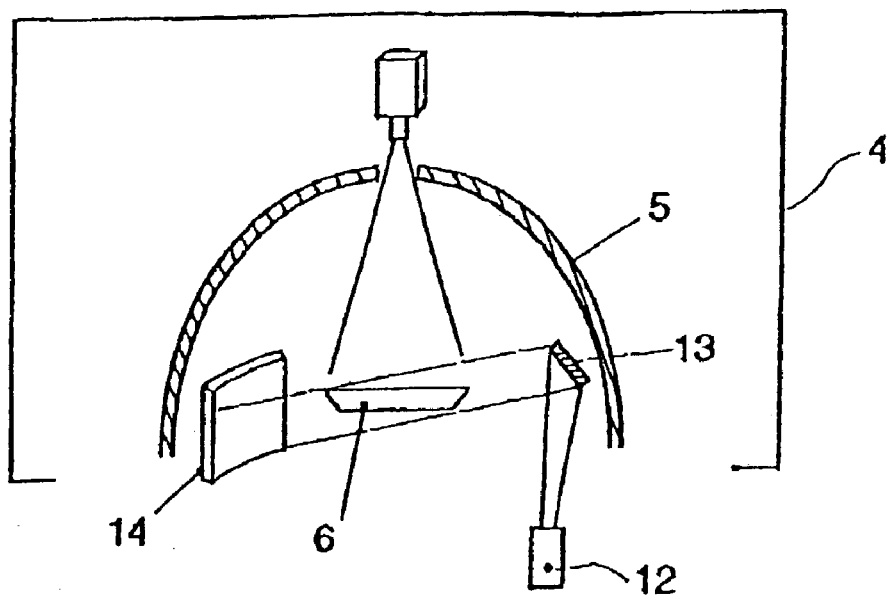
FIG. 4
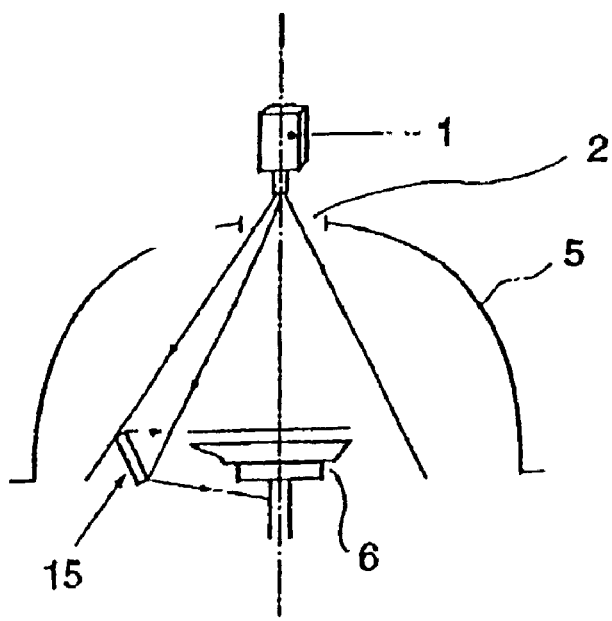
FIG. 5A
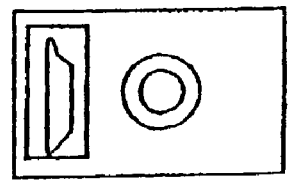
FIG. 5B
FIG. 5

FIG. 6A
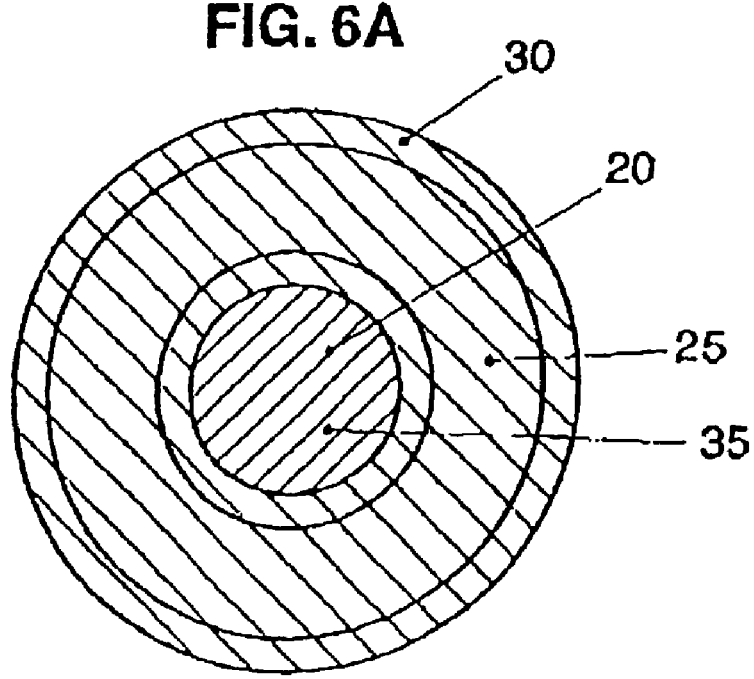
FIG. 6B
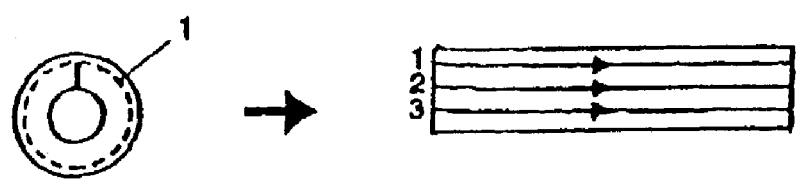
FIG. 6D
FIG. 6C
FIG. 6

FIG. 7A
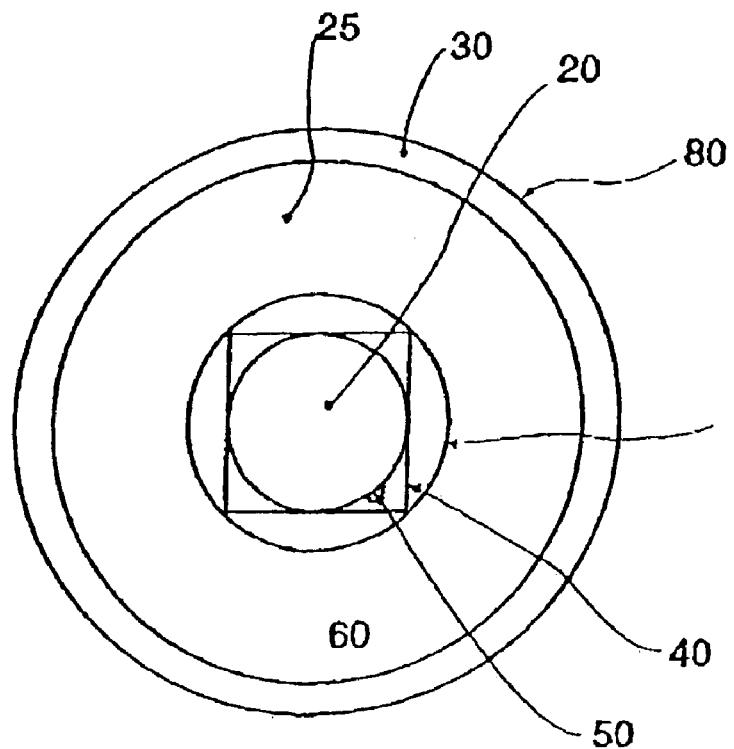
FIG. 7D
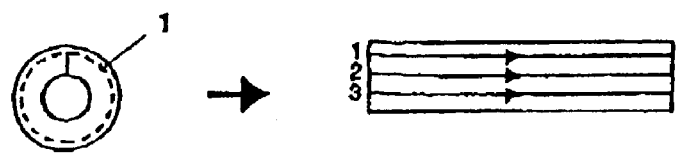
FIG. 7B
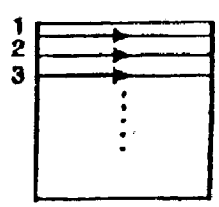
FIG. 7C
FIG. 7

FIG. 11A
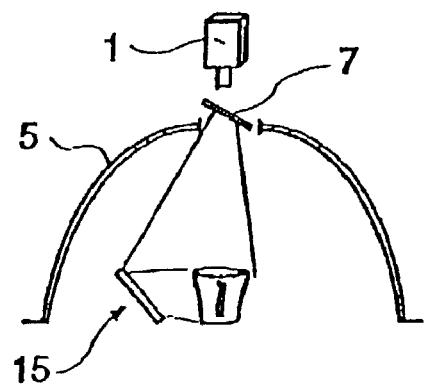
FIG. 11C
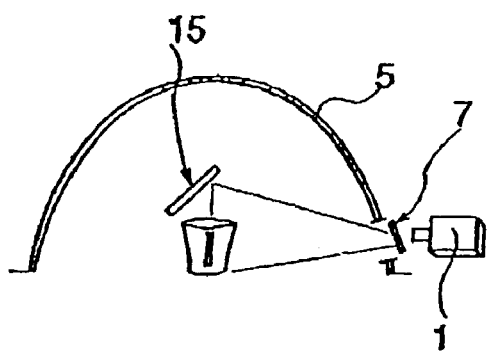
FIG. 11B
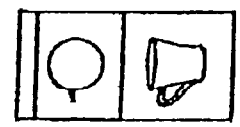
FIG. 11D
FIG. 11

FIG. 12(b)
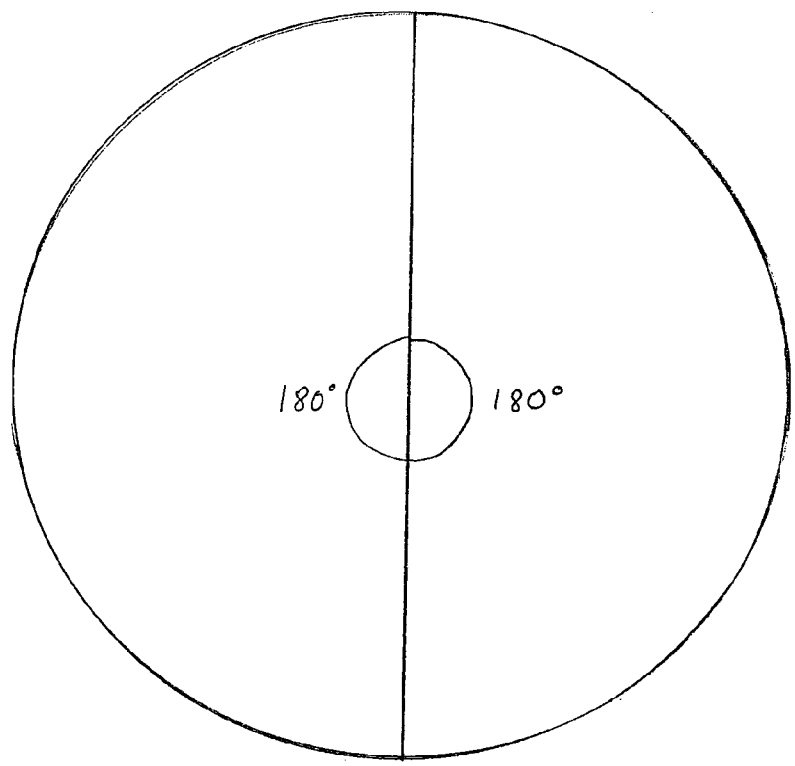
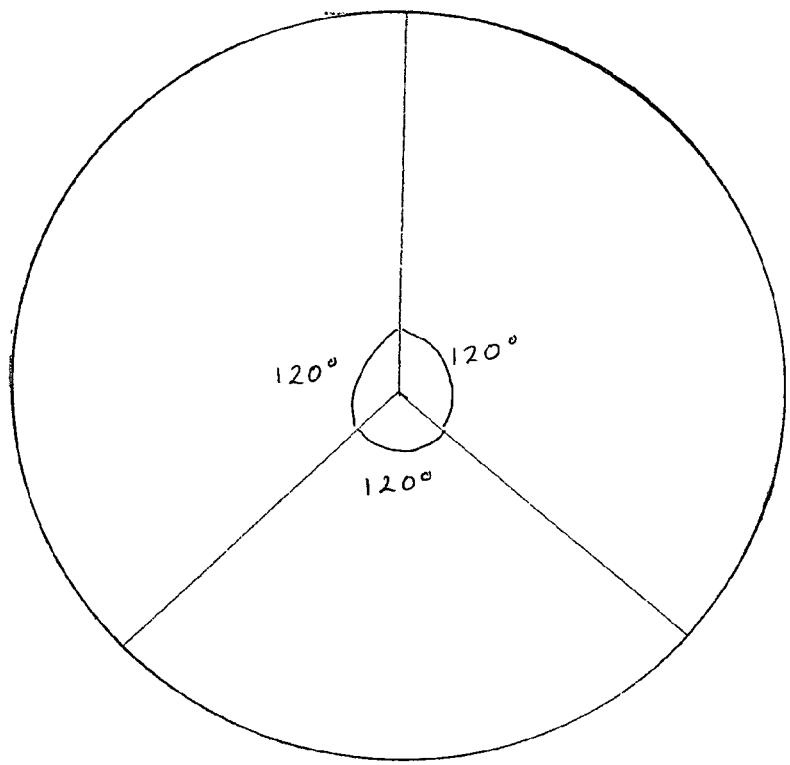
FIG 12(a)

DEVICE AND METHOD FOR OPTICAL CONTROL UNDER DIFFUSE ILLUMINATION AND OBSERVATION MEANS OF CROCKERY ITEMS OR ANY GLAZED CERAMIC PRODUCTS

The present invention relates to the technical field of inspecting the appearance of glazed or enameled pieces, and, generally, glazed ceramic pieces of complex shapes.

The invention relates particularly to a method and apparatus for enabling plates, cups (e.g. teacups, coffee cups, etc.), or any other object that can be similar to these two main shapes, to be inspected automatically.

"Similar to" is used here to indicate that the invention relates to uses for any products, including products lying outside the field of crockery, having shapes, surfaces, and relief, edging, etc. comparable to those of plates and cups, and made of a comparable material, i.e. a material posing the same type of technical problem as the technical problem given below.

Throughout the present invention, any reference to a "plate" or to a "cup" or to an element or piece of "crockery" is in no way limiting but rather, unless otherwise indicated, covers all of the other products encompassed in the above-defined generality.

Current State of the Art

Inspecting appearance by industrial viewing is an activity that is undergoing development in certain industries. The techniques and the equipment are developed and specialized to various extends depending on the size of the corresponding markets.

In the ceramic industry in the broadest sense, developments have been made and equipment is available on the market for certain products such as wall or floor tiles, and, to a lesser extent, roof tiles.

To date, on the market, there is no equipment for automatically inspecting crockery, i.e. plates, cups, serving dishes, coffeepots, teapots, vases, etc.

And yet, the proportion of the pieces leaving the kiln that have defects varies in the range 5% to 20% depending on the quality required by the manufacturer. As a result, sorting is essential. All of the efforts made for totally mastering the manufacturing method or "process" at temperatures often in excess of 1,000° C. have never succeeded in significantly improving the defect percentages.

Currently, throughout the world, such sorting is performed manually and is based on the physiological characteristic that the human eye is adapted to identifying "unusual" elements, probably because of the "warning" function of vision. Naturally, such work is tedious, especially when inspecting plates, which represent the largest proportion of output; assessment of defects is subjective, and therefore subject, to interpretation and variation; the sorting quality depends to a large extent on the state of tiredness of the operator.

An automated system thus procures improved objectivity, absence of tiredness, and a much higher throughput.

Current equipment designed for inspecting tiles, and that, in some cases, combines systems for illuminating the pieces as they advance rapidly, associated with an inspection camera, are not suitable at all for crockery. The shapes, the color, the shine, and the type of defect are all radically different.

Technical Problem

The difficulty lies in the fact that the type of product in question is very shiny, and thus any light source might generate spots that dazzle the camera, or that illuminate the product non-uniformly, making digital processing more random.

In addition, detecting white spots on a product that is already white presents a genuine difficulty for video technicians.

Finally, the product is of shape and of dimensions that only complicate matters further.

Products of the crockery type, such as coffeepots, teapots, and vases combine all of the difficulties encountered in optical inspection:

shininess of the surface;

white surface;

shapes having numerous incidences; and defects in the form of white spots on white backgrounds.

In addition, the production series of hollow articles, such as numerous pieces of crockery, such as, in particular, coffee pots, teapots, and vases, are much smaller and automation is much more complex, which renders it impossible to make a facility that is cost-effective.

Prior Art

In the prior art, light sources are known that provide uniform illumination over a certain area and at a certain distance, such as the LabSphere™ equipment, for calibrating and ground testing of sensors for satellites, for brightness measurements, radiant energy measurements, and the like. Uniform radiance is obtained over a distance of from 1 cm to 1 m, for example.

"Integration spheres" are also known that develop very diffuse illumination for inspecting objects. The principle consists in placing the object in the sphere or in the immediate vicinity of a portion of sphere, in illuminating the object via an opening provided in the sphere, or even in placing lighting inside the sphere, and in observing via another opening also provided in the sphere, optionally by using a semi-reflective strip. Products implementing those principles are proposed by Northeast Robotics™ for industrial video inspection of small products of complex shape and of various degrees of shininess.

Such systems have been adapted with a central opening enabling the field of an inspection camera to pass through.

Other equipment is also known that is rectangular block shaped and that emits uniform illumination, such as the DOAL-50-LED™ equipment, illuminating along the observation axis by using a semi-reflective strip.

Homogeneous, isotropic illumination systems are also known, such as the equipment of the illumination company Technologies Inc.™, for illuminating surfaces for the purpose of detecting defects or details. That equipment is used in numerous branches of industry to perform automatic video inspection of a wide variety of products.

Annular or surface illumination systems are also known that operate at high frequencies, greater than 25 kHz.

Thus, diffuse illumination systems are commercially available that are designed for small shiny pieces, using semi-reflective strips or integration spheres, but in different configurations, and that, in addition to an unsuitable scale factor, do not make it possible to provide inspection that is sufficiently high-performance and multi-purpose, and that satisfies the acute technical problem posed.

Such systems were not designed to inspect pieces of crockery that are relatively large in size and that are concave or convex to various extents, and are unsatisfactory as regards the required detectivity. In addition, they operate on a single principle.

As indicated above, numerous systems for inspecting ceramic tiles are also known.

The Qualitron™ equipment by System Ceramics™ performs special illumination associated with a special camera, for recognizing the tone classification code, or any downgrading.

The Tile Select™ equipment by Expert System™ illuminates (also at the outlet of the kiln as does the preceding equipment) the rapidly advancing pieces by means of a plurality of lamps, with inspection by a central camera.

The CeraVision™ equipment by Massen Machine Vision Systems™ operates by reflection, on the principle that a surface defect modifies the light signal received by the camera, in particular by diffusing the reflected light in a plurality of directions as a function of the defect.

All those items of equipment are dedicated to examining a flat product in which the defects that are specific to that product are sought. The illuminations, the algorithms, the handling of the products, and their shapes are radically different from those of crockery. For example, only the top face of a tile is inspected, whereas plates and other similar pieces of crockery require inspection of both faces and inspection of the edge.

Patent WO 96/24084 describes the use of sets of mirrors making it possible (by appropriately choosing the optical paths) to achieve a composite representation of an object of complex shape, in two dimensions only, the object nevertheless being seen by means of the set of mirrors from a plurality of inspection points situated around the object.

Patent WO 98/52087 similarly describes a set of reflectors which give an image of the object from a plurality of viewing points.

Patent WO 98/48243 describes inspecting the surface of an object by means of a glancing light source and of a sensor for sensing the reflected light, since a defect modifies the reflected light signal.

Patent EP 0 756 152 describes a method for inspecting the surface state of parts having reflective surfaces, in particular for inspecting the roughness of polished parts. The polished part is illuminated via a "pattern plate", and the reflection in the form of a plane pattern towards a detector is observed. Examining the contrasts in the pattern gives access to the roughness.

In certain alternatives of the prior art, glancing incident light is used.

Thus, no system of the prior art has been designed for pieces of crockery and the like, quality control currently still being performed by visual inspection by operators who are specially trained, but who are subject to errors or to tiredness, and whose inspection throughput is limited.

SUMMARY OF THE INVENTION

The invention relates mainly to methods for illuminating and observing the type of products in question, and of digitally processing the images in order to show up and identify defects, of whatever type: large or tiny black spots, white spots on a shiny white plate, edge or base cracks, base polishing defects, shape defects, glazing defects, stamp printing defect, etc., i.e. "multi-purpose" methods that are fully effective even in critical cases such as when there are a combination of complex shapes, of shininess, and of white-on-white defects, unlike the prior art.

Through its original design, the present invention makes it possible to use certain systems known from the prior art and to have them co-exist even thought they have hitherto been deemed to be contradictory, and to incorporate other systems, with the surprising and currently unknown result of achieving quality control concerning defects that are particularly difficult to detect and on pieces of complex shapes, such as elements or pieces of crockery, and of achieving this in an industrially cost-effective manner, in spite of the small series involved.

These methods and apparatuses apply mainly to white glazed ceramic tableware, but also to colored glaze.

In the general concept of the present invention, an inspection method is implemented for inspecting the surfaces of ceramic tableware/pieces of ceramic crockery (and the like, as defined in the general definition given in the introduction), said method being characterized in that:

A—the product is illuminated by overall or zone-by-zone diffuse illumination; and B—the product is observed using one or more observation means, by causing the overall diffuse illumination or the localized diffuse illumination coming from at least one diffuse illumination zone adapted to make at least a selected portion of the product shiny to reflect off said product towards said one or more observations means.

The combination of these two parameters is essential for genuine quality control to be achieved, such quality control being much more difficult to achieve than detecting defects such as black spots on a white background, for example.

In a first implementation option, diffuse, homogeneous, and isotropic illumination is effected (point A) on the entire piece and at least one zone of the product illuminated in this way is observed (point B).

In a second implementation option, limited and localized diffuse illumination is effected (point A) in one or more particular zones, and the reflected image of said illumination is observed (point B) on the product.

A major advantage of the invention is that it makes it possible to implement both options in a single item of equipment, which offers obvious industrial advantages.

The first option (overall diffuse illumination of the piece) produces a reflected image of medium tone, making it possible to reveal well certain types of defects, while the second option (localized illumination of at least a portion of the piece by at least one localized zone of diffuse illumination) makes it possible to bring closer the light/shade limit of the defect to be detected, and to obtain higher detectivity; this makes it possible to detect defects that are very difficult to detect, in particular pinholes in the glazing, or "shallow-sloping" depressions in the glazing, and the like.

In a particular embodiment, observation is optionally also performed by accessory means such as means delivering glancing illumination, and mirrors for reflecting at least a portion of the image of the product, in particular the image of one or more portions that are not visible to the main observation means because they are masked, e.g. by the product itself.

In a first preferred alternative of the invention, the method is performed in two stages.

In another alternative, the method is performed in two or more stages, typically with a plurality of successive illumination sequences.

In a second alternative of the invention, the method is performed in one stage only, by using additional optical multiplexing means.

In a non-limiting embodiment, said optical multiplexing is achieved by illuminations of different colors and corresponding filters, on the one or more observation means.

The person skilled in the art can understand that it is possible to make advantageous use of all of the technical possibilities of the camera; for example, it can be advantageous to zoom in on a particular zone of the product under examination, and to examine said zone only.

The invention applies in particular to ceramic tableware products, such as, typically, plates, cups, saucers, serving dishes or various objects whose shapes are similar to the shapes of the above-mentioned products; the above-defined general concept makes it possible both to illuminate the product in identical manner in all directions, but also to illuminate it in a defined zone that is observed by reflection, and, in secondary manner, it also makes it possible to integrate additional known techniques such as glancing illumination or multi-view mirrors into these illumination means.

It is possible to perform inspections of the "geometric" type. For the person skilled in the art, such inspections cover dimensional measurements such as diameter measurements, checking for out-of-roundness, etc., or measuring the height of the rim of a plate, which, by rotating the piece, gives access to detection of any "warping" of the piece (viewed by the plate "wobbling"); or else measuring the height of the base, or detecting warping by projecting an inclined laser beam onto the piece in combination with rotating the piece, and analogous measurements or inspections well known to the person skilled in the art.

This novel type of illumination eliminates all of the reflections and variations of light, thereby making detectivity of any different-color defect much higher, which solves all of the problems left unsolved by the prior art.

The observation of the product is preferably performed by at least one optical camera, or by the human eye, optionally with assistance from an accessory optical system.

In yet another particular embodiment, the observation is performed by two or more cameras.

First Option with "Overall" Diffuse Illumination

In a particular embodiment, the piece is placed in a closed (or partially open) enclosure made of an opaque diffusing material (in particular having an opaque white inside wall) or made of a translucent or frosted material, which enclosure homogenizes the light by reflection off the inside walls, and the illumination is performed by at least one source outside said enclosure, by allowing the illumination beam to penetrate via at least one opening provided for this purpose, and/or by at least one of the sources optionally disposed inside the enclosure, these external or internal sources being positioned such as to project their light beams towards said inside surface of said enclosure.

In yet another particular and preferred embodiment, said material of the enclosure is translucent or frosted.

In yet another particular and preferred embodiment, in particular when said material of the enclosure is translucent or frosted, one or more illumination sources are disposed outside the enclosure.

In yet another particular embodiment, the sources are placed under the enclosure, which covers the piece to be inspected at least partially and preferably totally.

In yet another particular embodiment, said enclosure has a dome (or a comparable surface that is spherical or hemispherical or substantially spherical or hemispherical, spherical or hemispherical oblate, or indeed spherical or hemispherical deformed into a cone, an ellipsoid, or a deformed ellipsoid, and other comparable shapes that are all designated in the present application by "dome") which itself has an opening making it possible to insert the piece, and at least one opening making it possible to allow the light reflected by the piece to pass through towards the one or more external observation means, in particular the camera(s).

The more convex the product to be inspected, the more closed the dome is.

The "dome" may also be cylindrical or rectangular block shaped, and such forms are included in the definition of "dome".

The bottom of the dome is preferably white or clear in color, translucent or opaque, with or without a light source, or else dark in color or black in order to create a contrast depending on what inspection is to be performed.

As indicated above, said bottom is optionally provided with one or more openings capable of and provided for allowing the product through and/or for allowing the light beams from the sources through to the inside wall of the dome.

The assembly is preferably hooded by means of an opaque material whose inside tends to distribute the illumination homogeneously, e.g. with white paint.

The camera is preferably placed at the pole of the dome, and points towards the main face of the product, through an opening provided in the dome.

In an alternative, the camera is placed inside the dome in full or in part, and it is then made optically invisible by suitable combinations of light-diffusing screens and of semi-reflective strips, the resulting assembly forming a hood around the camera that prevents unwanted reflections off the camera but that allows the reflected image of the piece to pass through to the lens.

The product to be examined is placed inside the dome, preferably in its central or bottom portion if the pole points upwards.

In a preferred alternative of the invention, in the localized reflection observation mode, the dome is inclined relative to the product (or else the product is inclined relative to the dome), or else observation means that are offset in inclination are added, or any other equivalent means are implemented that make it possible to achieve relative inclination, so that the illuminating diffuse zone does not include the location of the camera or the location of the optical system.

In a preferred embodiment, the piece to be examined is rotated under the dome and the camera zooms in on a zone; the combination of the rotation and of the zoom make it possible to examine the entire piece with magnification.

In yet another particular embodiment, an enclosure made of a translucent diffusing material is used as the dome, and said external illumination is performed by at least one, and preferably a plurality of light sources placed around the enclosure that covers the piece.

The illumination is then performed by transmission through the translucent and diffusing wall of the dome.

In yet another particular embodiment, the illumination is performed by a plurality of light sources distributed uniformly around said enclosure.

In an entirely preferred embodiment, the overall illumination direction is centripetal.

In yet another particular embodiment, the light sources are distributed in directions that are substantially centripetal and thus directed towards the center of the dome, in arbitrary uniform patterns such as, for example, in parallel lines, in a staggered pattern, and analogous layouts forming uniform distribution relative to the dome.

Such configurations are easily accessible to the person skilled in the art who can imagine numerous options.

In an advantageous embodiment, a light beam coming from a known light source is inserted into the dome, optionally by means of an additional mirror, under glancing incidence on the product.

In an entirely preferred embodiment, a semi-reflective strip is inserted between the cameras and the dome in order to mask the virtual images of the lenses in the product under inspection, and optionally other such strips are inserted to mask the image of any object inserted into the dome or of any opening provided in the dome, e.g. mirrors, additional lamps, and the like.

Second Option with "Zone-By-Zone" Diffuse Illumination

In yet another particular embodiment, the method is implemented by means of lamps or light sources and/or of known mecano-optical apparatus in order to illuminate at least one zone of the dome or of the diffusing screen.

The zone(s) may be of any different shapes, be they circular, elliptical or annular, solid or hollow, of different sizes, and of uniform or non-uniform shapes and dimensions, depending on the case in question.

It is thus possible to use a single zone, or a plurality of zones and then to conjugate together the illuminating and observed zones in question.

By way of non-limiting example, it is thus possible to illuminate diffusely a "rim" of a plate by a properly centered small circular zone, or to lo illuminate diffusely the annular edge of the "basin" of the plate, or else to combine the two illuminations in order to study the two portions of the piece simultaneously.

It is also possible to combine a plurality of circular zones on different portions of the rim, e.g. two or three 180° or 120° zones. This improves the rapidity of inspection of a piece, but more powerful processing means must be provided.

It is also possible to combine one or more circular zones with one or more rings, or square zones, etc.

The person skilled in the art can imagine all of the possible combinations using his or her own knowledge and the present description, depending on the particular piece to be inspected.

It is possible to combine all this with rotation of the piece, in order to cover the entire surface in question.

Alternatively, or in combination with the above, it is possible to project a known image on one or more "zones", the known image being, for example a grid of Cartesian or polar co-ordinates, or a "pattern plate", an array of points, of lines, etc. serving to show in the virtual image the optical and shape defects of the product inspected in reflection mode.

In this second implementation option, it is possible to use the same particular embodiments as those described with reference to the first option.

In a preferred alternative of the invention, the light sources are electrically powered from the three-phase network between phase and neutral, the sources being firstly uniformly distributed over each electrical phase and secondly uniformly distributed over the periphery of the dome. This is to smooth the ripple effect of the network by mixing light beams: each elementary zone of the dome thus receives the light from at least three different illuminations, each powered by a different electrical phase.

The invention also provides a method for optically inspecting the appearance of glazed ceramic products, performed in reflection mode with one light zone conjugate with the observed zone on the product being reflected.

This method consists in observing the virtual image in the product of a diffuse intense light zone situated or created on the diffusing dome.

Preferably, it is possible to form said zone by at least one light source placed above the dome made of a diffusing and translucent material.

The shape of the zone is conjugate with the shape of the observed zone on the piece so that said piece is seen as uniformly shiny and bright, and so that the other portions of the product are seen in dark manner, thus showing up the defects well. The better the two zones are conjugated together, the finer the detection.

In addition, this type of illumination tends to magnify the defects, and thus to improve the fineness of detection. The illuminated zone is defined as being the zone of the screen that would be illuminated if the camera were replaced by a source of light projected on the zone of the product to be inspected.

As indicated above, it is possible to combine the use of a plurality of zones of different shapes, dimensions, etc. optionally in combination with rotation of the piece.

The invention also provides an inspection method as defined above and in which two domes (or a plurality of domes) are used successively, by feeding in the products, pivoting them or turning them over, and removing them automatically by means of known mechanical means, in order to inspect the two or more faces of each of the glazed ceramic products successively.

In an alternative of the invention, when a plurality of successive domes are used, the piece is examined without using zooming in under at least one of the domes, and at least one particular zone of the piece is examined, under at least one of the other domes, with zooming in on at least one particular zone of the piece (e.g. a zone in which, for technical reasons, it is more difficult to detect defects), with or without rotation of the piece.

It is also possible to use a plurality of domes, one of which serves to inspect the piece in the first-option (overall diffuse illumination) and another of which serves to inspect the piece in the second option (diffuse illumination zone-by-zone).

It is also possible to equip the various domes with various items of accessory equipment, depending on the particular needs, such as mirrors, dimensional or geometrical measurement means, other cameras equipped with different lenses, filters, etc., with a system of illumination by means of a laser beam, or any other type of illumination.

Naturally, the person skilled in the art can combine these options and alternatives at will, with no particular difficulty.

The invention also provides apparatus suitable for implementing the above method.

In the general concept of the present invention, apparatus for inspecting the surfaces of ceramic tableware/pieces of ceramic crockery (and analogous objects, as defined in the general definition given by way of introduction) is characterized in that it includes means for:

A—illuminating the product by overall or zone-by-zone diffuse illumination; and

B—observing the product using one or more observation means, by causing the overall diffuse illumination or the localized diffuse illumination coming from at least one diffuse illumination zone adapted to make at least a selected portion of the product shiny to reflect off said product towards said one or more observations means.

In a first implementation option, diffuse, homogeneous, and isotropic illumination is effected (point A) on the entire piece and at least one zone of the product illuminated in this way is observed (point B).

In a second implementation option, limited and localized diffuse illumination is effected (point A) in one or more particular zones, and the reflected image of said illumination on the product is observed (point B).

In a first preferred alternative of the invention, the apparatus includes means for operating in two stages.

In a second alternative of the invention, the apparatus includes means for operating in one stage only, by using additional optical multiplexing means.

In a non-limiting embodiment, said optical multiplexing is achieved by illuminations of different colors and corresponding filters, on the one or more observation means.

In a particular embodiment, the apparatus optionally further includes accessory observations means such as means delivering glancing illumination, and mirrors for reflecting at least a portion of the image of the product, in particular the image of one or more portions that are not visible to the main observation means because they are masked, e.g. by the product itself.

In a particular embodiment, the means for observing by reflection preferably comprise at least one optical camera, or means of observation by the human eye, optionally with assistance from an accessory optical system.

In yet another particular embodiment, the apparatus includes two or more cameras.

In a particular embodiment, the means for performing diffuse illumination include a closed (or partially open) enclosure made of an opaque diffusing material (in particular having an opaque white inside wall), which enclosure homogenizes the light by reflection off the inside walls, and the illumination is performed by at least one source outside said enclosure, by allowing the illumination beam to penetrate via at least one opening provided for this purpose, and/or by at least one of the sources optionally disposed inside the enclosure, these external or internal sources being positioned such as to project their light beams towards said inside surface of said enclosure.

In yet another particular and preferred embodiment, said material of the enclosure is translucent or frosted.

In yet another particular and preferred embodiment, in particular when said material of the enclosure is translucent or frosted, one or more illumination sources are disposed outside the enclosure.

In yet another particular embodiment, the sources are placed under the enclosure, which covers the piece to be inspected at least partially and preferably totally.

In yet another particular embodiment, the enclosure has a dome (or a comparable surface that is spherical or hemispherical or substantially spherical or hemispherical, spherical or hemispherical oblate, or indeed spherical or hemispherical deformed into a cone, an ellipsoid, or a deformed ellipsoid, and other comparable shapes that are all designated in the present application by "dome") which itself has an opening making it possible to insert the piece, and at least one opening making it possible to allow the light reflected by the piece to pass through towards the one or more external observation means, in particular the camera(s).

The more convex the product to be inspected, the more closed the dome is.

The "dome" may also be cylindrical or rectangular block shaped, and such forms are included in the definition of "dome".

The bottom of the dome is preferably white or clear in color, translucent or opaque, with or without a light source, or else dark in color or black in order to create a contrast depending on what inspection is to be performed.

In yet another particular embodiment, the sources are placed under the enclosure, which covers the piece to be inspected at least partially and preferably totally.

The assembly is preferably hooded by means of an opaque material whose inside tends to distribute the illumination homogeneously, e.g. with white paint.

The camera is preferably placed at the pole of the dome, and points towards the main face of the product, through an opening provided in the dome.

In an alternative, the camera is placed inside the dome in full or in part, and it is then made optically invisible by suitable combinations of light-diffusing screens and of semi-reflective strips, the resulting assembly forming a hood around the camera that prevents unwanted reflections off the camera but that allows the reflected image of the piece to pass through to the lens.

In a preferred alternative of the invention, in the localized reflection observation mode, the apparatus includes a dome inclined relative to the product (or else means for inclining the product relative to the dome), or else it includes observation means that are offset in inclination, or any other equivalent means that make it possible to achieve relative inclination, so that the illuminating diffuse zone does not include the location of the camera or the location of the optical system.

In yet another particular embodiment, said external illumination is performed by at least one and preferably more light sources.

In yet another particular embodiment, an enclosure made of a translucent diffusing material is used as the dome, and said external illumination is performed by at least one, and preferably a plurality of light sources placed around the enclosure that covers the piece.

The illumination is then performed by transmission through the translucent and diffusing wall of the dome.

In yet another particular embodiment, the illumination is performed by a plurality of light sources distributed uniformly around said enclosure.

In an entirely preferred embodiment, the overall illumination direction is centripetal.

In yet another particular embodiment, the light sources are distributed in one direction or in a plurality of parallel directions, or in arbitrary uniform patterns such as, for example, in a staggered pattern, and analogous layouts.

In an advantageous embodiment, a light beam coming from a known light source is inserted into the dome, optionally by means of an additional mirror, under glancing incidence on the product.

In an entirely preferred embodiment, a semi-reflective strip is inserted between the cameras and the dome in order to mask the virtual images of the lenses in the product under inspection, and optionally other such strips are inserted to mask the image of any object inserted into the dome or of any opening provided in the dome, e.g. mirrors, additional lamps, and the like.

The invention also provides apparatus for optically inspecting the appearance of glazed ceramic products, performed in reflection mode with one light zone conjugate with the observed zone on the product being reflected.

This apparatus has an intense light zone (defined as the zone of the screen that would be illuminated if the camera were replaced with a source of light projected on the zone of the product to be inspected) situated on the diffusing dome. The shape of the intense light zone is conjugate with the shape of the observed zone on the piece so that said piece: is seen as uniformly shiny and bright, and so that the other portions of the piece are seen in dark manner, thus showing up the defects well.

In yet another particular embodiment, the method is implemented by means of lamps or light sources and/or of known mecano-optical apparatus in order to illuminate a zone of the dome or of the diffusing screen, firstly with different shapes, be they circular, elliptical or annular, solid or hollow, of different sizes, in order to conjugate together the zones in question; and secondly, with a known image, e.g. a grid of Cartesian or polar co-ordinates, an array of points, or lines, etc., . . . serving to show up in the virtual image the optical and shape defects of the product inspected in reflection mode.

The zone(s) may be of any different shapes, be they circular, elliptical, or annular, solid or hollow, of different sizes and of uniform or nonuniform dimensions, depending on the case in question.

It is thus possible to use a single zone, or a plurality of zones and then to conjugate together the zones in question.

By way of non-limiting example, it is thus possible to illuminate diffusely a "rim" of a plate by a properly centered small circular zone, or to illuminate diffusely the annular edge of the "basin" of the plate, or else to combine the two illuminations in order to study the two portions of the piece simultaneously.

It is also possible to combine a plurality of circular zones on different portions of the rim, e.g. two or three 180° or 120° zones. This improves the rapidity of inspection of a piece, but more powerful processing means must be provided.

It is also possible to combine one or more circular zones with one or more rings, or square zones, etc.

The person skilled in the art can imagine all of the possible combinations using his or her own knowledge and the present description, depending on the particular piece to be inspected.

It is possible to combine all this with rotation of the piece, to cover the entire surface in question.

In a preferred alternative of the invention, the light sources are electrically powered from the three-phase network between phase and neutral, the sources being firstly uniformly distributed over each electrical phase and secondly uniformly distributed over the periphery of the dome. This is to smooth the ripple effect of the network by mixing light beams: each elementary zone of the dome thus receives the light from at least three different illuminations, each powered by a different electrical phase.

The invention also provides inspection apparatus as defined above which includes two successive domes (or a plurality of successive domes), and means for feeding in the products, pivoting them or turning them over, and removing them automatically, in order to inspect the two or more faces of each of the glazed ceramic products successively.

It is also possible to use a plurality of successive domes, one of which serves to inspect the piece in the first option (overall diffuse illumination) and another of which serves to inspect the piece in the second option (diffuse illumination zone-by-zone).

It is also possible to equip the various domes with various items of accessory equipment, depending on the particular needs, such as mirrors, dimensional or geometrical measurement means, other cameras equipped with different lenses, filters, etc., with a system of illumination by means of a laser beam, or any other type of illumination.

Naturally, the person skilled in the art can combine these options and alternatives at will, with no particular difficulty.

A non-limiting example of apparatus of the invention includes a translucent screen that is in the form of a dome that is spherical or partially spherical, or cylindrical or rectangular block shaped, and a lamp directed towards the screen in a zone whose reflection in the glazed ceramic product is observed by one or more cameras or optical systems. The diffusing dome or screen is preferably white, but it may be colored for certain pieces having colored glazing, with a black-and-white or color camera depending on the type of inspection desired.

In preferred alternative of the invention, the dome is inclined relative to the product so that the illuminated zone does not include the location of the camera or of the optical system. As defined in this claim, either the dome or the product can be moved.

The invention also provides apparatus as described above and in which a light beam coming from a known light source is inserted into the dome, optionally by means of an additional mirror, under an angle of incidence glancing off the product so that that portion of the beam which has not interfered with the product does not illuminate the diffusing screen or dome, optionally by adding a dark screen. This type of configuration makes it possible to detect well white spots on convex surfaces and base defects.

The invention also provides apparatus as described above and in which one or more preferably retractable mirrors are inserted into the bottom portion of the dome in order to add a profile view of the product in the field of vision of the camera(s).

In a preferred embodiment, a semi-reflective strip is inserted between the cameras and the dome in order to mask the virtual images of the lens(es) in the product under inspection, and optionally other strips are inserted aimed at masking the image of any object that can be inserted in the dome or of any opening provided in the dome, e.g. mirrors, additional lamps, etc.

The invention also provides a method as described above and specially adapted to inspecting optionally glazed ceramic products that are circularly symmetrical, the method consisting in performing computer processing in two stages by means of the method described above, the first stage being for the central zone of the product, such as the basin or bottom of the plate, for example, with a conventional algorithm, over a square or rectangular zone, scanning the pixels of the zone of the image from left to right and from top to bottom, the second stage being for the peripheral zone, such as the rims, the "marly", or the base of the plate, for example, processed as a ring or as portions of ring that is firstly "unrolled", and on which the processing is effected in lines from left to right and from bottom to top, each line corresponding to a zone of constant radius relative to the center of the piece.

Accessory interpolation and re-adjustment tools for interpolation and re-adjustment of the zones on the edges of the piece conventionally improve the detectivity associated with this method.

The apparatus of the invention further includes mechanical means making it possible to cause the pieces to advance at high speed under the dome(s), so as to place each object under the set of illumination means and of observation means, for a time that is sufficient for the inspection.

Such mechanical means are described in outline below. On the basis of this non-limiting mechanical embodiment, the person skilled in the art is capable of implementing other mechanisms without any difficulty.

Other objects and advantages of the invention will be better understood on reading the following description with reference to the accompanying drawings, in which:

FIG. 1 is a diagrammatic view of general apparatus of the invention, FIG. 1A showing a system operating by transmission through the wall of the dome, and FIG. 1B showing the same system operating by reflection off the dome;

FIG. 4 is a diagrammatic view of apparatus of the invention in which glancing light generator apparatus is inserted in the dome;

Figure 8:
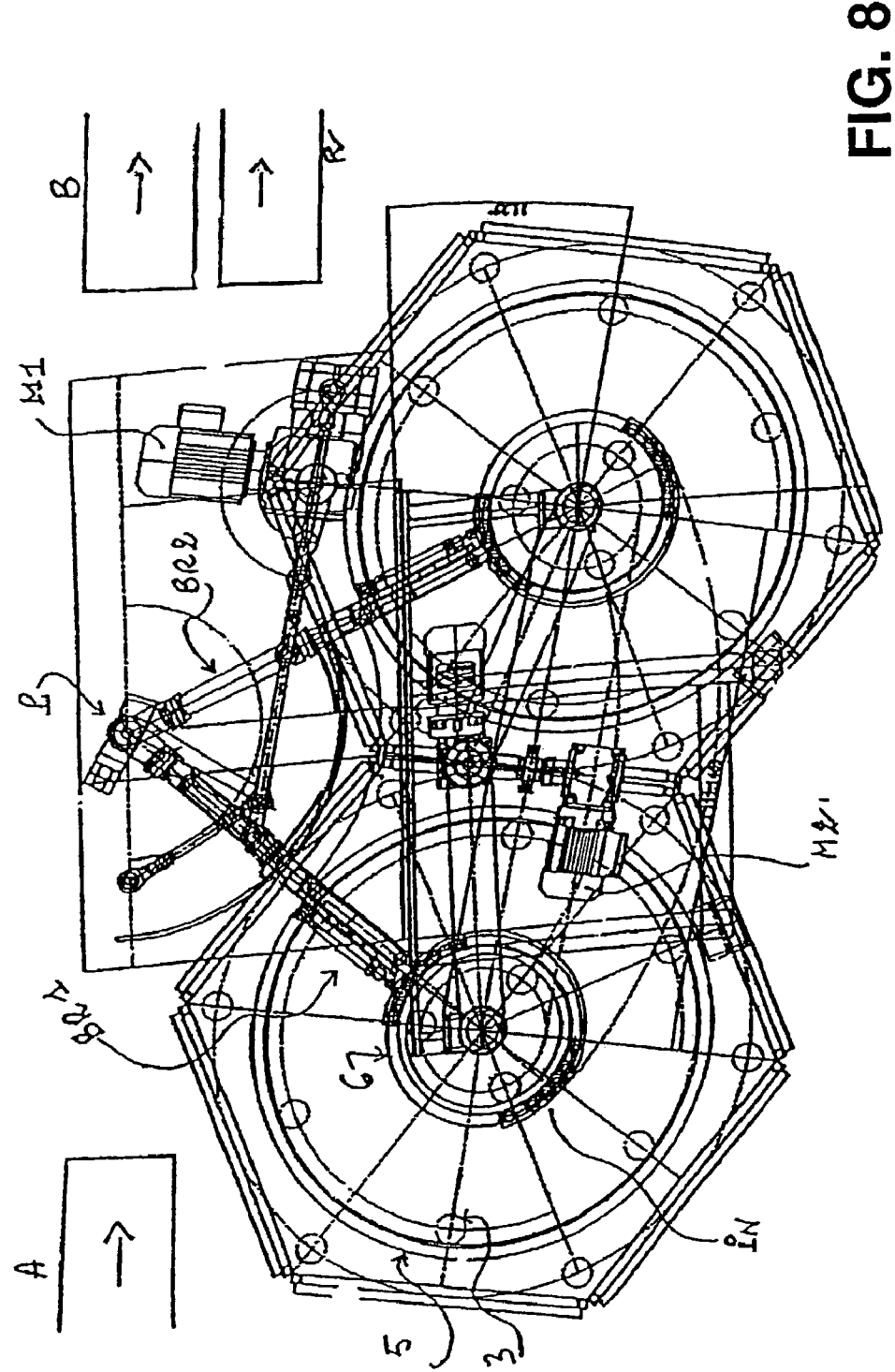
Figure 9:
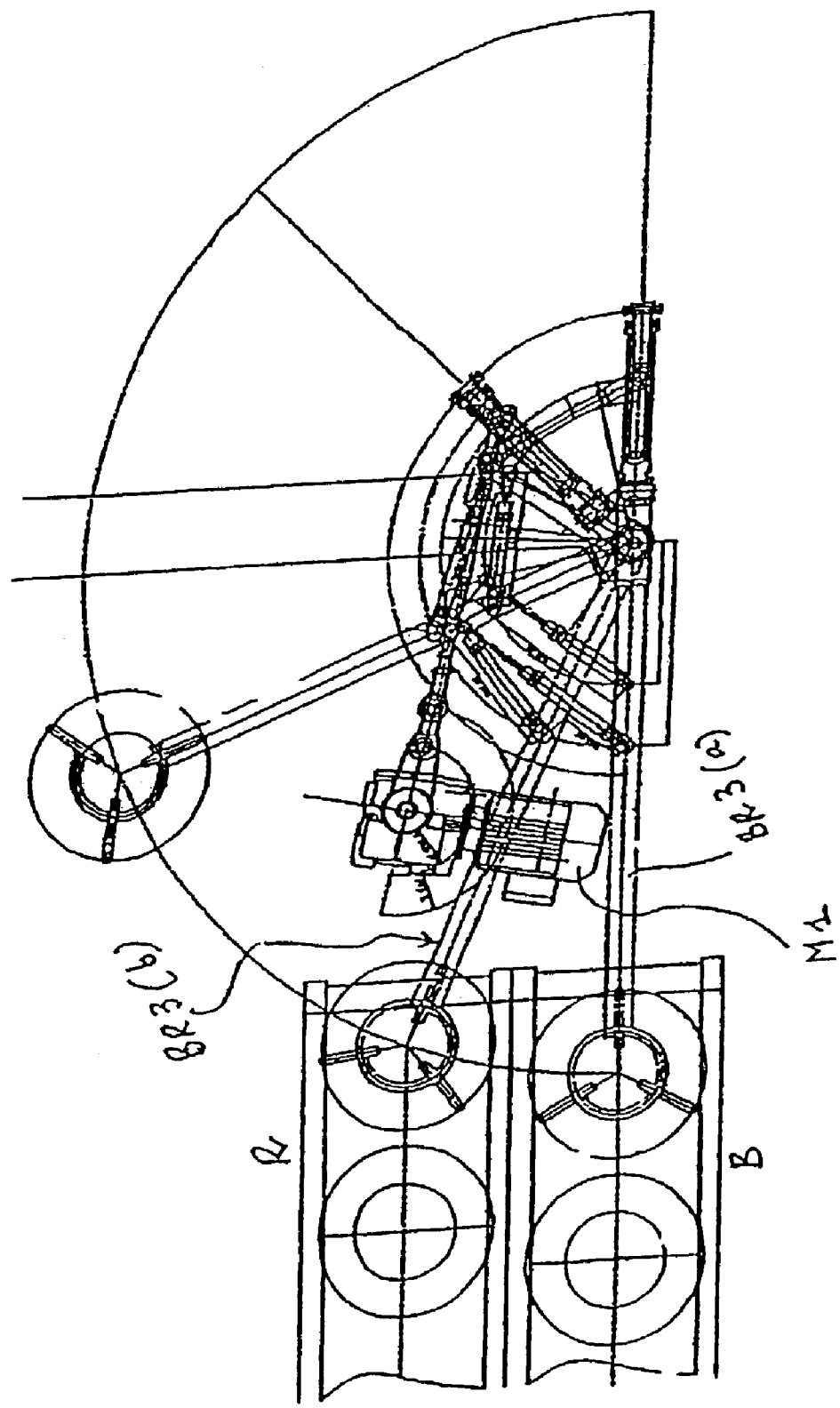
Figure 10:
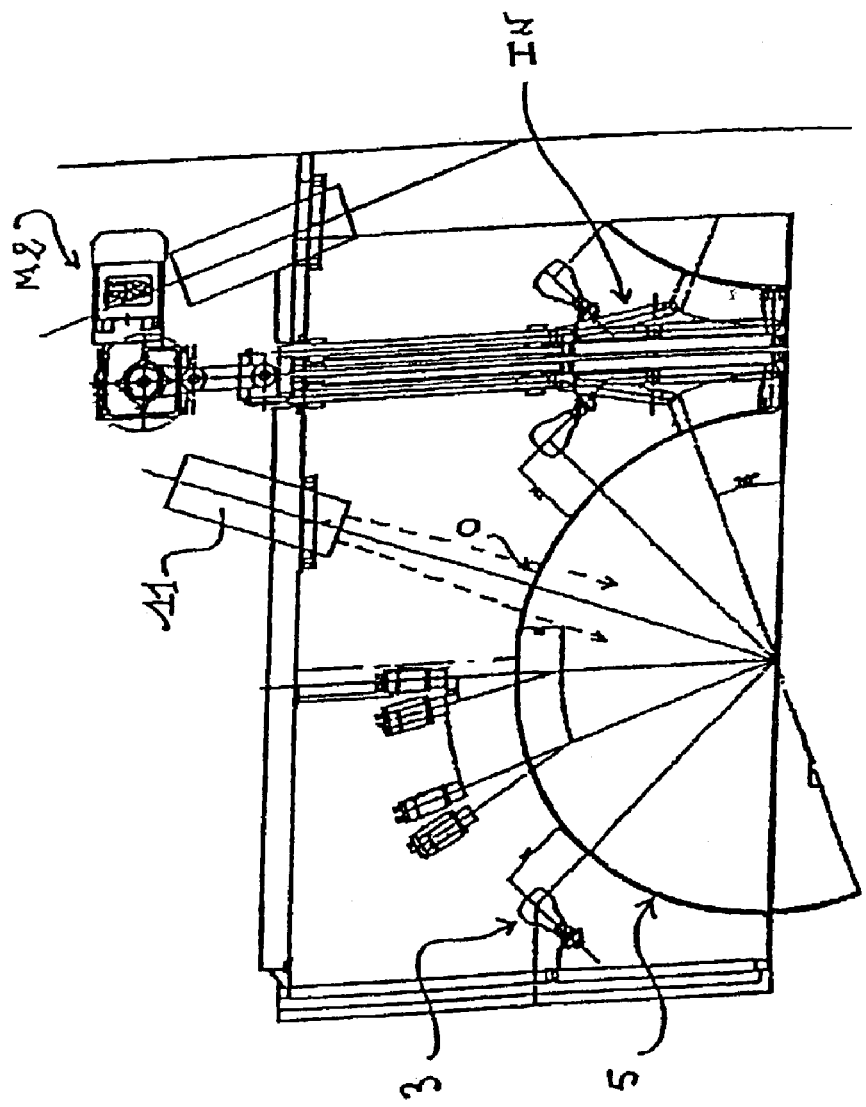

FIG. 5 (which is made up of FIGS. 5A and 5B, FIG. 5B showing the image as seen by the camera) is a diagrammatic view showing apparatus of the invention (FIG. 5A) in which one or more optionally retractable mirrors are placed around the piece to send back to the camera the images of the hidden portions of the piece;

FIG. 6, which is made up of FIGS. 6A, 6B, 6C, and 6D, is a diagrammatic view showing the method of the invention in which the processing is performed in two stages;

FIG. 6A shows how the piece (a plate in this example) is subdivided into a bottom, a rim, a peripheral zone and a central zone, in illuminated zones, and in concentric circles;

FIG. 6B shows the ring corresponding to the illuminated peripheral zone;

FIG. 6D shows the ring as "unrolled";

FIG. 6C shows the disk formed by the illuminated or "processed" central zone;

FIG. 7, which is made up of FIGS. 7A, 7B, 7C, and 7D is a diagrammatic view showing the method of the invention in which processing is performed in two stages;

FIG. 7A shows how the piece (a plate in this example) is subdivided into a bottom, a rim, a peripheral zone, and a central zone, as in FIG. 6, except in that the central zone is illuminated or "processed" in a square;

FIG. 7B shows the ring corresponding to the illuminated peripheral zone;

FIG. 7D shows the ring as "unrolled";

FIG. 7C shows the square formed by the illuminated central zone;

FIG. 8 shows a non-limiting mechanical embodiment making it possible to cause the pieces to advance through a machine including apparatus of the invention, including two domes;

FIG. 9 is a supplement to FIG. 8, showing more clearly the arms which, at the outlet of the machine, deposit the pieces either on the conveyor for the pieces that have passed inspection, or on the conveyor for the rejects;

FIG. 10 is a side view showing the machine having two domes, and in particular the apparatus making it possible to incline the dome; and FIG. 11, which is made up of FIGS. 11A to 11D, shows inspection of a cup in two alternatives of positioning of the camera, and by using a mirror.

FIGS. 12(a) and 12(b) illustrate three 120° zones and two 180° zones, respectively, defined on a surface of a piece of crockery by the diffuse illumination.

Accompanying FIG. 1A, which shows the overall diffuse lighting option, with, in this example, light sources uniformly distributed above a dome, shows that the pieces 6 pass under a translucent dome 5 that diffuses by transmission the light emitted by light sources 3 placed outside. The diffused light is reflected by the piece, in particular towards the camera 1 through a suitable orifice 2 provided in the dome facing the camera. The resulting assembly is encased by a hood 4. The means for causing the pieces to advance under the dome are not shown. Only the inlet orifice is shown (an outlet orifice naturally exists in the direction of advance of the pieces).

Accompanying FIG. 1B shows the same configuration as FIG. 1A except that the light sources are placed under the dome and that the light is diffused by a white opaque dome, by being reflected towards the piece.

Figure 2:
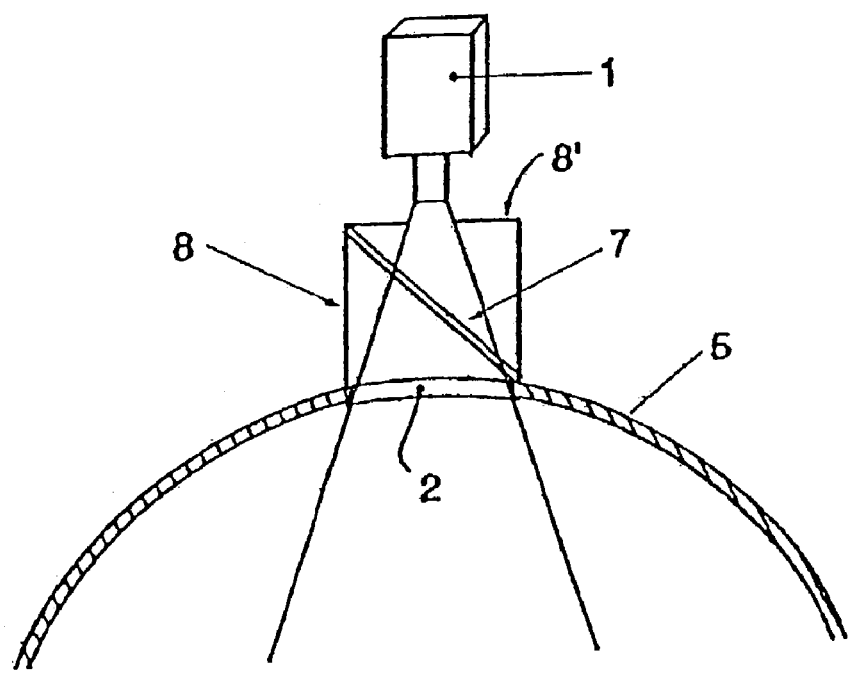
FIG. 2 is a diagrammatic view showing how a semi-reflective strip is inserted under the optical system of the camera of FIG. 1.

In FIG. 2, the apparatus is as shown in FIG. 1, except that a semi-reflective strip 7 is inserted that is inclined using principles known in optics, and placed in a hood that is translucent and light in color (8) on one side of the strip and that is opaque and dark in color (8') on the other side, and that serves as a support for said strip.

Figure 3:
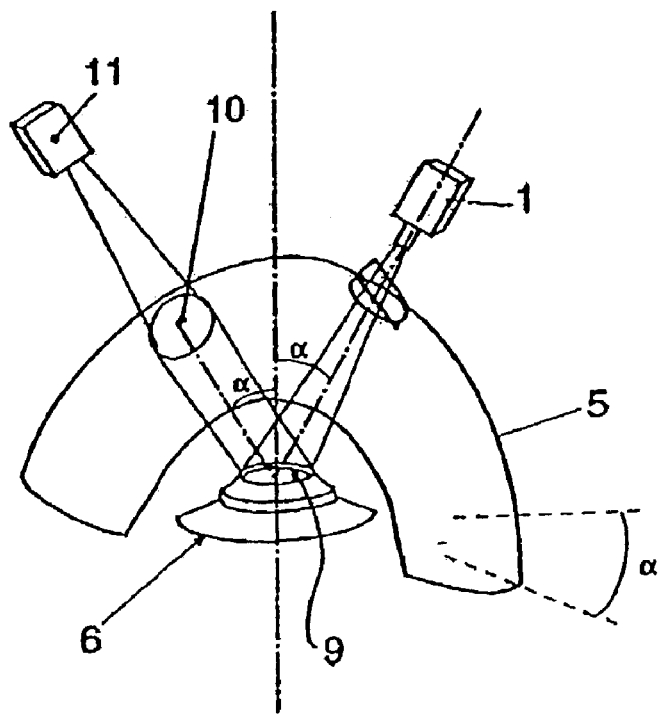
FIG. 3 is a diagrammatic view showing apparatus of the invention for implementing the variant method having a light zone conjugate with the observed zone.

In FIG. 3, which shows the option of diffuse illumination zone-by-zone, by means of a single zone in this example, an intensely illuminated zone 10 is formed on the diffuser dome 5 (which, in this figure, is shown in the position inclined at an angle_relative to the horizontal; said zone is adapted in dimensions and in geometry to illuminate a zone 9 (the bottom 9 of a plate 6 in this example) referred to as the "conjugate" zone, and the image of said zone 9 is returned selectively towards the camera 1.

FIG. 4 shows a generating system for generating glancing light and which consists of a lamp 12 (placed for convenience under the plane of the object) which illuminates a mirror 13 which reflects the light in the form of a beam f of glancing light; the glancing beam f illuminates the piece 6, thereby delivering additional indications for the lens of the camera 1, and is then absorbed by a light-absorbing screen 14 serving to avoid unwanted reflection of the beam f towards the piece or towards the camera.

In FIG. 5, a mirror 15 is placed that is inclined so as to return the image of a zone not visible by the camera (the side of a plate in this example) to the camera in compliance with the rules known from optics. The camera can thus inspect (FIG. 5B) simultaneously the top of the plate and one of its sides; to inspect the entire side, two symmetrical mirrors or even three or four mirrors are naturally provided, each of which covers an angular sector of 120° or of 90°.

FIG. 6 shows the situation in which the center of the piece (the bottom 20 and the central zone 35 of the plate in this example) and the peripheral zone 30 and the rim 25 of the plate are illuminated in two stages. The first illumination, gives a disk (FIG. 6C) that can be analyzed by an algorithm, and the second illumination gives a ring that can also be analyzed (FIGS. 6B and 6D).

FIG. 7 shows the same method as FIG. 6, except that the central zone is illuminated but processed using a square computing zone.

In FIG. 7, 25 represents the rim of the plate, 20 represents the bottom, 30 represents the peripheral zone, 80 represents the outer limit of the inspection ring, 70 represents the edge of the plate, 60 represents the "marly" which marks the limit between the basin and the rim of the plate, 40 represents the processing square of the inspection zone, and 50 represents the inner limit of the inspection ring.

FIG. 8 shows a plan view of a machine having two domes of the invention. In this naturally non-limiting embodiment, it can be seen that the two domes are adjoining with a central inclination mechanism that can be seen more clearly in FIG. 10. The pieces are brought by the feed conveyor A, they are then picked up by one of the arms BR1 which clamps them by means of symmetrically clamping pincers PN that have wheels not referenced but clearly visible in the Figure. A motor M1 makes it possible to move the arms BR1 and BR2 (as well as a third arm BR3 not shown in the figure), the three arms being mounted to pivot about a pivot P. The piece 6 is examined under the dome 5 illuminated by the light sources 3, and is then grasped by the arm BR2 which brings it under the second dome for a second inspection. Suction cups assist in the manipulation in a manner that the person skilled in the art can easily understand. After the second inspection, an arm B3 (FIG. 9) grasps the piece-and, as a function of the result of the inspections, deposits it either on the "accepted pieces" conveyor (position BR3(a) of the arm) or on the "refused pieces" conveyor (position BR3(b) of the arm BR3). FIG. 10 shows a dome 5 that is inclined (at 20° in this example) by a mechanism IN driven by a motor M2, also visible in FIG. 2. FIG. 9 shows the case when a zone of the translucent dome is illuminated by a lamp 11. Such a machine can process up to 1,200 pieces of crockery per hour.

FIG. 11 shows two alternatives for inspecting a cup using a mirror for full observation, using the principle already explained above, the references being identical to those of FIG. 7.

FIG. 11A shows a mode of positioning the camera 1 above the dome 5, with a mirror 15 that returns to the camera the image of the side of the piece (a cup in this example). FIG. 11B shows the same observation with different positioning of the camera 1. In both cases, a semi-transparent strip 7 is interposed "under" the lens of the camera.

FIGS. 11B and 11D respectively show the images returned by the piece (cup) and by the mirror 15 to the camera, for the positioning shown respectively in FIGS. 11A and 11C.

The invention also relates to apparatus as described above, characterized in that it includes, in particular, pivotally-mounted arms for picking up the piece and putting it down under at least one dome, then optionally for transferring said piece to the following dome, and optionally means for inclining the piece relative to at least one dome, or for inclining at least one dome relative to the piece.

The invention is not limited to the applications described above, and the person skilled in the art is capable of adapting the methods and apparatus described above in order to extend the uses of them to inspecting bathroom products such as shower trays, toilet pans, urinals, bidets, wash basins, sinks, etc. by recreating the above-described illumination methods locally or overall.

In addition, in a particular embodiment, use is advantageously made of the means for inspecting glazed products as described above to inspect as well the graphics and/or the location of the stamp, particularly if it is a glaze-covered stamp, or any other glazed or decorated product.

The invention claimed is:

1. A method for inspecting a surface of a piece of ceramic crockery, the method comprising the steps of:
    positioning the piece within an enclosure, the enclosure comprising:
        an interior surface,
        at least one first opening, and
        at least one second opening separate and distinct from the at least one first opening;
    illuminating the piece by diffuse illumination using an illumination means, the illumination means comprising:
        at least one light source disposed outside the enclosure, and
        means for delivering at least a portion of illumination from the at least one light source; and
    observing the piece with an observation means and at least one mirror to detect a defect in the surface of the piece,
    wherein the illumination from the at least one light source penetrates the enclosure via the at least one second opening of the enclosure,
    wherein the illumination from the at least one light source is homogenized by reflecting off of the interior surface of the enclosure to form the diffuse illumination,
    wherein light reflected from the surface of the piece passes through the at least one first opening towards the observation means, and
    wherein the at least one mirror reflects an image of the piece to the observation means.

2. A method according to claim 1, wherein the observing step is performed by at least one optical camera and optionally with assistance from an accessory optical system.

3. A method according to claim 1, wherein the observation means is two or more cameras.

4. A method according to claim 1, wherein the means for delivering at least a portion of illumination from the at least one light source delivers the at least a portion of the illumination in a direction that is substantially parallel to the surface of the piece.

5. A method according to claim 1, wherein the illuminating the piece step is performed in at least two stages with a plurality of successive illumination sequences.

6. A method according to claim 5, wherein a first stage of the illuminating the piece step is performed with an optical multiplexing means.

7. A method according to claim 1, wherein the diffuse illumination is effected on an entirety of the piece, thereby illuminating at least one zone.

8. A method according to claim 1, wherein the enclosure further comprises a floor, wherein the at least one second opening is formed in the floor of the enclosure, and wherein the at least one light source is positioned under the floor of the enclosure.

9. A method according to claim 1, wherein the enclosure is formed from one of an opaque, translucent, and frosted material.

10. A method according to claim 9, wherein the at least one light source is positioned under the enclosure, and wherein the enclosure partially covers the piece.

11. A method according to claim 1, wherein the enclosure further comprises a third opening, and wherein positioning the piece within the enclosure comprises inserting the piece through the third opening.

12. A method according to claim 8, wherein a the floor of the enclosure is of a color selected from the group consisting of white, clears translucent, opaque, dark, and black.

13. A method according to claim 12, wherein the enclosure is surrounded by a hood, wherein the hood is formed from an opaque material, and wherein an interior surface of the hood distributes the diffuse illumination homogeneously therein.

14. A method according to claim 1, wherein the observation means is inclined relative to the illumination means.

15. A method according to claim 11, wherein the observation means is at least one optical camera, wherein the piece is rotated under the enclosure, and wherein the at least one camera zooms in on a portion of the piece.

16. A method according to claim 1, wherein the means for delivering is a mirror.

17. A method according to claim 1, wherein the diffuse illumination is localized on one or more zones of the piece, and
    wherein the one or more zones is observed.

18. A method according to claim 1, wherein the at least one light source is selected from the group consisting of a lamp and a meccano-optical apparatus to illuminate at least one zone within the enclosure.

19. A method according to claim 7, wherein the at least one zone is circular, elliptical, annular, solid, hollow, of different sizes, of uniform shapes, of non-uniform shapes, of uniform dimensions, or of non-uniform dimensions.

20. A method according to claim 7, wherein a plurality of zones is illuminated.

21. A method according to claim 1, further comprising a step of rotating the piece to cover an entire surface of the piece.

22. A method according to claim 17, further comprising projecting an image on the one or more zones of the piece, wherein the image is selected from a grid of Cartesian co-ordinates, polar co-ordinates, a pattern plate, an array of points, or an array of lines, and wherein optical and shape defects of the piece show up as a distortion in the protected image reflected from the surface of the piece.

23. A method according to claim 1, wherein the at least one light source is electrically powered by a three-phase network between phase and neutral, and wherein the at least one light source is uniformly distributed over each electrical phase.

24. A method according to claim 22, wherein the illumination of the at least one light source forms at least one diffuse intense light zone on the interior surface of the enclosure,
wherein the at least one diffuse intense light zone is reflected onto the surface of the piece to form a virtual image, and
wherein the light reflected from the surface of the piece toward the observation means corresponds to the virtual image.

25. A method according to claim 24, wherein the at one or more zones is a plurality of light zones of zones of different shapes and dimensions, and wherein the piece is optionally rotated.

26. A method according to claim 7, wherein the enclosure is a plurality of domes, wherein observing the piece occurs sequentially within the plurality of domes,
wherein the piece is fed into each of the plurality of domes, the piece is positioned within each of the plurality of domes, one or more faces of the piece is inspected within each of the plurality of domes, and the piece is removed from each of the plurality of domes, and wherein a mechanism automatically feeds, positions, and removes the piece from each of the plurality of domes.

27. A method according to claim 26, wherein the piece is examined without zooming under at least one of the plurality of domes, and at least one zone of the piece is examined, with zooming with or without rotation of the piece in another of the plurality of domes.

28. A method according to claim 1, wherein the piece is a glazed ceramic product, and wherein observing the piece comprises computer processing in two stages, wherein the first stage comprises scanning a first image of a central portion of the glazed ceramic product from left to right and from top to bottom of the image, and
the second stage comprises scanning a second image of a peripheral portion of the glazed ceramic product, from left to right and from bottom to top of the image, wherein each line of the image corresponds to a portion of the peripheral portion having a constant radius relative to the center of the piece.

29. A method according to claim 7, further comprising zooming in on a first zone of the at least one zone of the piece and examining the first zone only.

30. A method according to claim 1, wherein at least a portion of the image of the piece is an image of one or more portions of the piece that are not directly visible by the observation means.

31. A method according to claim 6, wherein the optical multiplexing means comprises illuminations of different colors and corresponding filters.

32. A method according to claim 1, wherein the enclosure totally covers the piece.

33. A method according to claim 1, wherein the enclosure is a dome and wherein the dome is spherical, hemispherical, substantially spherical, substantially hemispherical, spherical oblate, hemispherical oblate, spherical deformed into a cone, hemispherical deformed into a cone, ellipsoid, deformed ellipsoid, cylindrical, or rectangular-block shaped.

34. A method according to claim 1, wherein the observation means comprises at least one camera.

35. A method according to claim 1, wherein the enclosure is inclined relative to the piece.

36. A method according to claim 1, wherein the piece is inclined relative to the enclosure.

37. A method according to claim 20, wherein the plurality of zones comprises a plurality of circular zones combined on different portions of the piece.

38. A method according to claim 20, wherein the plurality of zones comprise two 180° zones or three 120° zones, or one or more circular zones combined with one or more rings or square zones.

39. A method according to claim 27, wherein one of the plurality of domes is used to inspect the piece under diffuse illumination, and wherein a second dome of the plurality of domes is used to inspect the piece under diffuse illumination zone-by-zone.

40. A method according to claim 39, wherein the plurality of domes includes accessory equipment comprising mirrors, dimensional or geometrical measurement means, or cameras equipped with lenses or filters.

41. A method according to claim 40, wherein the illumination means comprises a laser beam.

42. A method according to claim 28, wherein the glazed ceramic product is circularly symmetrical.

43. A method according to claim 28, wherein the central portion of the glazed ceramic product is a basin or bottom of a plate.

44. A method according to claim 28, further comprising accessory interpolation and re-adjustment tools for interpolation and re-adjustment of the peripheral portion of the glazed ceramic product.

45. A method according to claim 1, wherein the piece comprises ceramic tableware, plates, cups, saucers, or serving dishes.

46. A method according to claim 34, wherein the enclosure is a dome, and wherein the camera is placed on a pole of the dome and is directed towards a face of the piece through the at least one first opening.

47. A method according to claim 46, wherein at least a portion of the camera is placed inside the dome,
wherein the camera is made optically invisible by a mask comprising at least one of a light-diffusing screen and a semi-reflective strip, and
wherein the mask prevents unwanted reflections off the camera but allows light reflected from the piece to pass through to a lens of the camera.

48. A method according to claim 47, wherein the semi-reflective strip is inserted between the camera and the dome to mask virtual images of the lens in the piece.

49. Apparatus for inspecting a surface of a piece of ceramic crockery, comprising:
an enclosure comprising:
an interior wall,
at least one first opening, and
at least one second opening separate and distinct from the at least one first opening;
an illuminating means comprising at least one light source disposed outside the enclosure for providing illumination;
an observation means for observing a defect in the surface of the piece;
means for delivering at least a portion of the illumination; and
at least one mirror,
wherein the illumination from the at least one light source penetrates the enclosure via the at least one second opening,
wherein the illumination reflects off of the interior wall of the enclosure to form diffuse illumination,
wherein the diffuse illumination is reflected from at least a portion of the piece through the at least one first opening towards the observation means, and
wherein the at least one mirror reflects an image of the piece to the observation means.

50. Apparatus according to claim 49, further comprising a means for making the diffuse illumination homogeneous and isotropic, wherein the observing means observes at least one zone of the piece illuminated by the diffuse, homogeneous, and isotropic illumination.

51. Apparatus according to claim 49, wherein the means for delivering at least a portion of the illumination delivers the at least a portion of the illumination in a direction that is substantially parallel to the surface of the piece.

52. Apparatus according to claim 49, wherein the enclosure is formed from one of a translucent and frosted material.

53. Apparatus according to claim 49, wherein the enclosure is a dome, and wherein the dome further comprises a third opening, and wherein the piece is inserted through the third opening.

54. Apparatus according to claim 49, wherein the enclosure is a dome, wherein the observation means is a camera, and wherein the camera is provided on a pole on the dome and is directed towards a face of the piece through the at least one first opening.

55. Apparatus according to claim 49, wherein the observation means is inclined relative to the illuminating means.

56. Apparatus according to claim 53, further comprising a mechanical means to insert the piece under the dome through the third opening for a period of time sufficient to inspect the piece.

57. Apparatus according to claim 56, further comprising:
pivotally-mounted arms for picking up the piece, for putting down the piece under the dome through the third opening and optionally for transferring said piece to a second dome, and
inclining means for inclining the piece relative to the dome or for inclining the dome relative to the piece.

58. Apparatus according to claim 49, wherein the piece comprises plates, cups, saucers, or serving dishes.

59. Apparatus according to claim 54, wherein at least a portion of the camera is placed inside the domes,
wherein the camera is made optically invisible by a mask comprising at least one of a light-diffusing screen and a semi-reflective strip, and
wherein the mask prevents unwanted reflections off the camera but allows a reflected image of the piece to pass through to a lens of the camera.

60. Apparatus according to claim 49, wherein the observation means is adapted to inspect graphics, a stamp location, or a glaze-coated stamp of the piece.

* * * * *